United States Patent
Mongeon et al.

(10) Patent No.: US 6,988,000 B2
(45) Date of Patent: Jan. 17, 2006

(54) FORCED DECELERATION ALGORITHM FOR SYNCHRONIZATION OF ATRIAL CARDIOVERSION SHOCK AND TECHNIQUE FOR THE IMPLEMENTATION

(75) Inventors: Luc R. Mongeon, Minneapolis, MN (US); Thomas Sinner, New Brighton, MN (US)

(73) Assignee: Medtronic, Inc., Minneapolis, MN (US)

( * ) Notice: Subject to any disclaimer, the term of this patent is extended or adjusted under 35 U.S.C. 154(b) by 380 days.

(21) Appl. No.: 10/368,871

(22) Filed: Feb. 20, 2003

(65) Prior Publication Data

US 2003/0135242 A1    Jul. 17, 2003

Related U.S. Application Data

(62) Division of application No. 09/627,243, filed on Jul. 27, 2000, now abandoned.

(51) Int. Cl.
    *A61N 1/39*    (2006.01)
(52) U.S. Cl. ......................................... 607/5
(58) Field of Classification Search .................. 607/4, 607/5, 9, 14
    See application file for complete search history.

(56) References Cited

U.S. PATENT DOCUMENTS

| | | | |
|---|---|---|---|
| 4,232,679 A | 11/1980 | Schulman | |
| 4,375,817 A | 3/1983 | Engle et al. | |
| 4,384,585 A | 5/1983 | Zipes | |
| 4,572,191 A | 2/1986 | Mirowski et al. | |
| 4,587,970 A | 5/1986 | Holley et al. | |
| 4,726,380 A | 2/1988 | Vollmann et al. | |
| 4,726,877 A | 2/1988 | Fryd et al. | |
| 4,800,883 A | 1/1989 | Winstrom | |
| 4,830,006 A | 5/1989 | Haluska et al. | |
| 4,880,005 A | 11/1989 | Pless et al. | |
| 4,949,719 A | 8/1990 | Pless et al. | |
| 4,953,551 A | 9/1990 | Mehra et al. | |
| 5,107,850 A | 4/1992 | Olive | |
| 5,117,824 A | 6/1992 | Keimel et al. | |
| 5,161,527 A | 11/1992 | Nappholz et al. | |
| 5,163,427 A | 11/1992 | Keimel | |
| 5,188,105 A | 2/1993 | Keimel | |

(Continued)

FOREIGN PATENT DOCUMENTS

EP    0 594 274 A2    11/1993

(Continued)

OTHER PUBLICATIONS

Barold, et al., "Modern Cardiac Pacing", p. 727-743, 1985.

*Primary Examiner*—George R. Evanisko
(74) *Attorney, Agent, or Firm*—Daniel G. Chapik; Girma Wolde-Michael (57) ABSTRACT

Primarily, the invention relates to a safe delivery of atrial cardioversion pulses in complex cardiac therapy environments wherein cardiac events suggest, for example, rapid ventricular rates that would prevent a safe atrial cardioversion. The invention generally utilizes an algorithmic system in which a resultant R-R interval encountered subsequent to the delivery of a ventricular pacing pulse is decrementally scanned until an R-R interval is found that will yield a reliable sustained R-R interval. The sustenance of the R-R interval prolongation enables ventricular deceleration. Strategically selected timing windows are used to trigger a device response that is proper and tailored to the ventricular event detected during and within the timing windows. Further, the invention enables an atrial cardioversion synchronization method that allows for the safe delivery of atrial cardioversion pulses in the presence of very rapid ventricular rates.

12 Claims, 5 Drawing Sheets

U.S. PATENT DOCUMENTS

| | | |
|---|---|---|
| 5,193,536 A | 3/1993 | Mehra |
| 5,411,524 A | 5/1995 | Mehra |
| 5,411,525 A | 5/1995 | Swanson et al. |
| 5,464,431 A | 11/1995 | Adams et al. |
| 5,486,198 A | 1/1996 | Ayers et al. |
| 5,545,186 A | 8/1996 | Olson et al. |
| 5,560,369 A | 10/1996 | McClure et al. |
| 5,620,471 A | 4/1997 | Duncan |
| 5,674,249 A | 10/1997 | Coriolis et al. |
| 5,968,079 A | 10/1999 | Warman et al. |
| 6,081,745 A * | 6/2000 | Mehra ............ 607/4 |

FOREIGN PATENT DOCUMENTS

| | | |
|---|---|---|
| WO | WO 95/28987 A1 | 11/1995 |
| WO | WO 95/28988 A1 | 11/1995 |
| WO | WO 99/56823 A1 | 11/1999 |
| WO | WO 02/09810 A3 | 2/2002 |

* cited by examiner

FORCED DECELERATION ALGORITHM FOR SYNCHRONIZATION OF ATRIAL CARDIOVERSION SHOCK AND TECHNIQUE FOR THE IMPLEMENTATION

This is a division of application Ser. No. 09/627,243, filed Jul. 27, 2000, now abandoned.

FIELD OF THE INVENTION

The present invention relates to medical devices. Specifically, the invention relates to devices that treat tachyarrhythmias (rapid heart rhythms) and, more specifically, to methods for providing delivery of atrial cardioversion and defibrillation shocks at appropriate times relative to native atrial and ventricular depolarizations.

BACKGROUND OF THE INVENTION

It has long been recognized that synchronizing atrial and ventricular cardioversion pulses to native depolarizations in the chamber being treated improves efficacy of treatment. For example, synchronization of ventricular cardioversion shocks to sensed R-waves is disclosed in U.S. Pat. No. 4,375,817 issued to Engle et al. Synchronization of cardioversion shocks intended to treat atrial or ventricular tachycardia or fibrillation to detected R-waves is disclosed in U.S. Pat. No. 4,384,585, issued to Zipes. Similarly, synchronization of atrial cardioversion shocks to detected P-waves is disclosed in U.S. Pat. No. 4,572,191, issued to Mirowski et al.

Delivery of cardioversion or defibrillation shocks intended to terminate a tachyarrhythmia in one chamber may unfortunately induce a tachyarrhythmia in the other chamber. The risk associated with tachyarrhythmia induction in the ventricle is sufficiently great that it has long been recognized that atrial defibrillation pulses need to be timed to avoid the vulnerable period of the ventricle. The most common approach to accomplish this result has been to deliver the atrial defibrillation or cardioversion pulse closely synchronized to a sensed ventricular depolarization to avoid the associated ventricular vulnerable period, as disclosed in U.S. Pat. No. 4,384,585, issued to Zipes. It has also long been recognized that the vulnerable period following a ventricular depolarization may extend to include the subsequent ventricular depolarization in the presence of a sufficiently rapid ventricular rhythm. In such cases, there is no safe time to deliver a cardioversion pulse, as discussed in the article "Synchronous Intracardiac Cardioversion", by Zipes et al., published in *Modern Cardiac Pacing*, edited by Barold, Futura Publishing Co. 1985, pages 727–743.

Because cardioversion pulses synchronized to a ventricular rhythm that is too rapid may induce ventricular arrhythmias or fibrillation, implantable cardioverters have typically included some method to assure that a minimum R-R interval has elapsed as a prerequisite to delivery of a cardioversion shock. One such synchronization method which prevents delivery of a cardioversion pulse, synchronized to a ventricular rhythm which is too rapid, is to require that the shock be synchronized to a ventricular depolarization falling outside a defined refractory period that follows the preceding ventricular depolarization, as in the Model 7210 implantable transvenous cardioverter manufactured by Medtronic, Inc. While this device could sense ventricular depolarizations during this refractory period and would initiate a new refractory period following such depolarizations, it would not deliver cardioversion pulses synchronized to such depolarizations. As reflected in the above-cited article by Zipes et al, the transvenous cardioversion therapy provided by the model 7210 device could be employed to treat either ventricular or supraventricular tachyarrhythmias.

A more sophisticated method of synchronization to sensed R-waves is set forth in U.S. Pat. No. 5,486,198, in which a shock is delivered synchronized to an R-wave only if the interval between the R-wave and the immediately preceding R-wave is greater than or, no more than, a defined amount less than the immediately preceding R-R interval. Unfortunately, this method of synchronization to sensed R-waves, like those discussed above, does not allow for the safe delivery of an atrial cardioversion shock in the presence of too rapid a ventricular rate.

An alternative method for preventing the delivery of an atrial cardioversion shock during the ventricular vulnerable period is to deliver the shock after a defined interval that follows a preceding R-wave, in the absence of an intervening sensed ventricular depolarization-the defined interval being of sufficient duration to prevent delivery during the vulnerable period associated with the preceding R-wave. Such a synchronization method is disclosed in U.S. Pat. No. 5,411,524, issued to Mehra. As disclosed in the Mehra patent, the defined interval may vary as a function of the sensed ventricular rate, but it must be greater than a predefined minimum duration and thus is also unavailable in the presence of too rapid a ventricular rate.

An additional method to avoid delivery of a cardioversion pulse during the vulnerable period of a chamber of the heart is to pace the chamber and deliver the cardioversion pulse during the absolute refractory period following the pacing pulse. One such approach is also disclosed in U.S. Pat. No. 5,411,524 issued to Mehra, wherein an atrial cardioversion pulse is synchronized to a single ventricular pacing pulse and in U.S. Pat. No. 5,193,536, also issued to Mehra, wherein a ventricular cardioversion pulse is synchronized to the last of a series of ventricular pacing pulses. In both cases, the ventricular pacing escape interval is calculated to be less than the intervals separating intrinsic ventricular depolarizations. These methods unfortunately are not necessarily useful in the case of a ventricular rhythm that is so rapid as to render the synchronization to an overdrive ventricular pacing pulse unsafe.

SUMMARY OF THE INVENTION

The present invention relates to an implantable atrial defibrillator that provides for safe delivery of atrial cardioversion pulses even in the presence of a ventricular rate so rapid it would otherwise preclude safe atrial cardioversion. The device utilizes a phenomenon similar to one observed in bradycardia pacing, employing it in an atrial cardioversion synchronization method. In bradycardia pacing it has been observed that delivery of an overdrive ventricular pacing pulse closely timed to a sensed R-wave causes a prolonged R-R interval thereafter, much like the compensatory pause following a (Premature Ventricular Contraction) PVC. It has been previously determined in Ser. No. 09/135,480, filed Aug. 17, 1998 "Method and Apparatus for Treatment of Arrhythmias," that this phenomenon manifests itself even in the presence of atrial fibrillation. This fact, in turn, has allowed the development of an atrial cardioversion synchronization method that allows for the safe delivery of atrial cardioversion pulses in the presence of very rapid ventricular rates.

A device employing the method of the present invention monitors the R-R intervals in the presence of atrial fibrillation and calculates a mean R-R interval for the previous 10 intervals. This mean R-R interval is the reference interval to determine the percentage decrement required for the ventricular paced output that will cause a prolongation of the R-R interval. This algorithm is similar to the method described in the above-cited Mehra '524 patent, on expiration of which a ventricular pacing pulse is delivered. However, rather than immediately delivering an atrial cardioversion pulse synchronized to the delivered ventricular pacing pulse, the resultant R-R interval is decrementally scanned until an R-R interval is found that will yield a reproducible, forced and prolonged R-R interval. When found, the atrial defibrillation capacitor begins charging. When the charge is complete the presence of atrial fibrillation is reconfirmed. At that time, the forced deceleration algorithm is activated. The ventricle is paced at the automatically calculated and measured settings found prior to capacitor charging. To assure ventricular rate deceleration (interval prolongation), the algorithm uses three distinct and defined timing windows: 1) a programmable blanking period during which sensing is disabled to ensure the ventricular pacing pulse will not be sensed and a shock cannot be delivered; 2) a programmable abort and reset period during which the device monitors for sensed R-waves and, if one is sensed, the scheduled shock is aborted and the algorithm is reset; and 3) a shock synchronization period during which an atrial shock will be synchronized to a sensed R-wave falling within this period. Thus a ventricular event occurring within any of the three periods results in a separate and distinct response by the device.

DETAILED DESCRIPTION OF THE DRAWINGS

Figure 1:
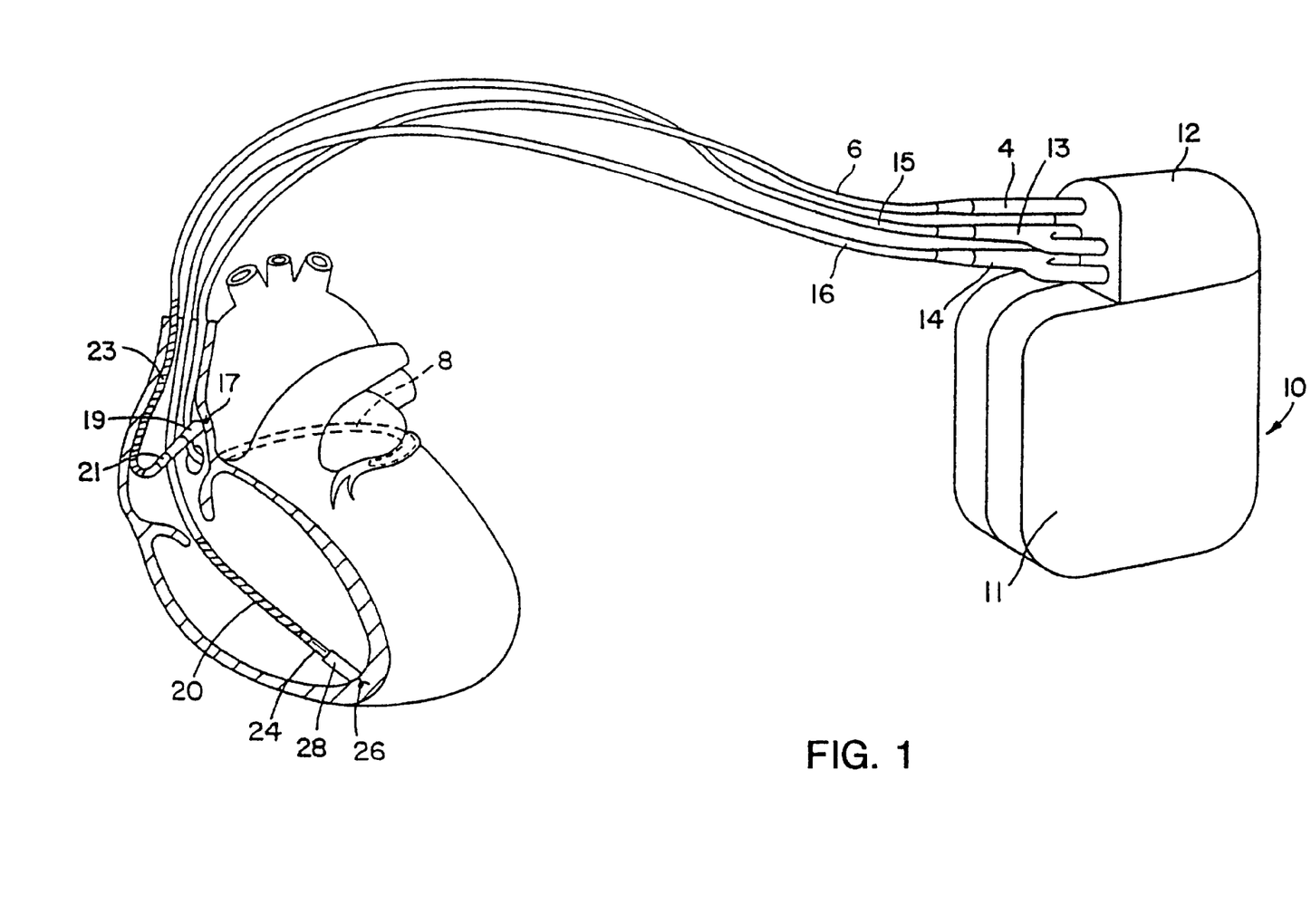
FIG. 1 illustrates a first embodiment of an implantable pacemaker/cardioverter/defibrillator of a type appropriate for use in practicing the present invention, in conjunction with a human heart.

FIG. 1 illustrates a defibrillator and lead set according to the present invention. The ventricular lead includes an elongated insulative lead body 16, carrying three concentric coiled conductors, separated from one another by tubular insulative sheaths. Located adjacent the distal end of the lead are a ring electrode 24, an extendable helix electrode 26, mounted retractably within an insulative electrode head 28, and an elongated coiled defibrillation electrode 20. Each of the electrodes is coupled to one of the coiled conductors within the lead body 16. Electrodes 24 and 26 are employed for cardiac pacing and for sensing ventricular depolarizations. At the proximal end of the lead is a bifurcated connector 14 that carries three electrical connectors, each coupled to one of the coiled conductors. The defibrillation electrode 20 may be fabricated from platinum, platinum alloy or other materials known to be usable in implantable defibrillation electrodes and may be about 5 cm in length.

The atrial/SVC lead includes an elongated insulative lead body 15, carrying three concentric coiled conductors, separated from one another by tubular insulative sheaths, corresponding generally to the structure of the ventricular lead. Located adjacent to the J-shaped distal end of the lead are a ring electrode 21 and an extendable helix electrode 17, mounted retractably within an insulative electrode head 19. Each of the electrodes is coupled to one of the coiled conductors within the lead body 15. Electrodes 17 and 21 are employed for atrial pacing and for sensing atrial depolarizations. An elongated coiled defibrillation electrode 23 is provided, proximal to electrode 21 and coupled to the third conductor within the lead body 15. Electrode 23 preferably is 5 cm in length or greater and is configured to extend from the SVC toward the tricuspid valve. At the proximal end of the lead is a bifurcated connector 13 that carries three electrical connectors, each coupled to one of the coiled conductors.

The coronary sinus lead includes an elongated insulative lead body 6, carrying one coiled conductor, coupled to an elongated coiled defibrillation electrode 8. Electrode 8, illustrated in broken outline, is located within the coronary sinus and great vein of the heart. At the proximal end of the lead is a connector plug 4 that carries an electrical connector, coupled to the coiled conductor. The coronary sinus/great vein electrode 8 may be about 5 cm in length.

An implantable pacemaker/cardioverter/defibrillator 10 is shown in combination with the leads, with the lead connector assemblies 4, 13 and 14 inserted into the connector block 12. Optionally, insulation of the outward facing portion of the housing 11 of the pacemaker/cardioverter/defibrillator 10 may be provided using an insulative coating, for example parylene or silicone rubber, as is currently employed in some unipolar cardiac pacemakers. However, the outward facing portion may instead be left uninsulated, or some other division between insulated and uninsulated portions may be employed. The uninsulated portion of the housing 11 optionally serves as a subcutaneous defibrillation electrode, used to defibrillate either the atria or ventricles. Other lead configurations and electrode locations may, of course, be substituted for the lead set illustrated. For example, atrial defibrillation and sensing electrodes might be added to either the coronary sinus lead or the right ventricular lead instead of being located on a separate atrial lead, allowing for a two-lead system.

Figure 2:
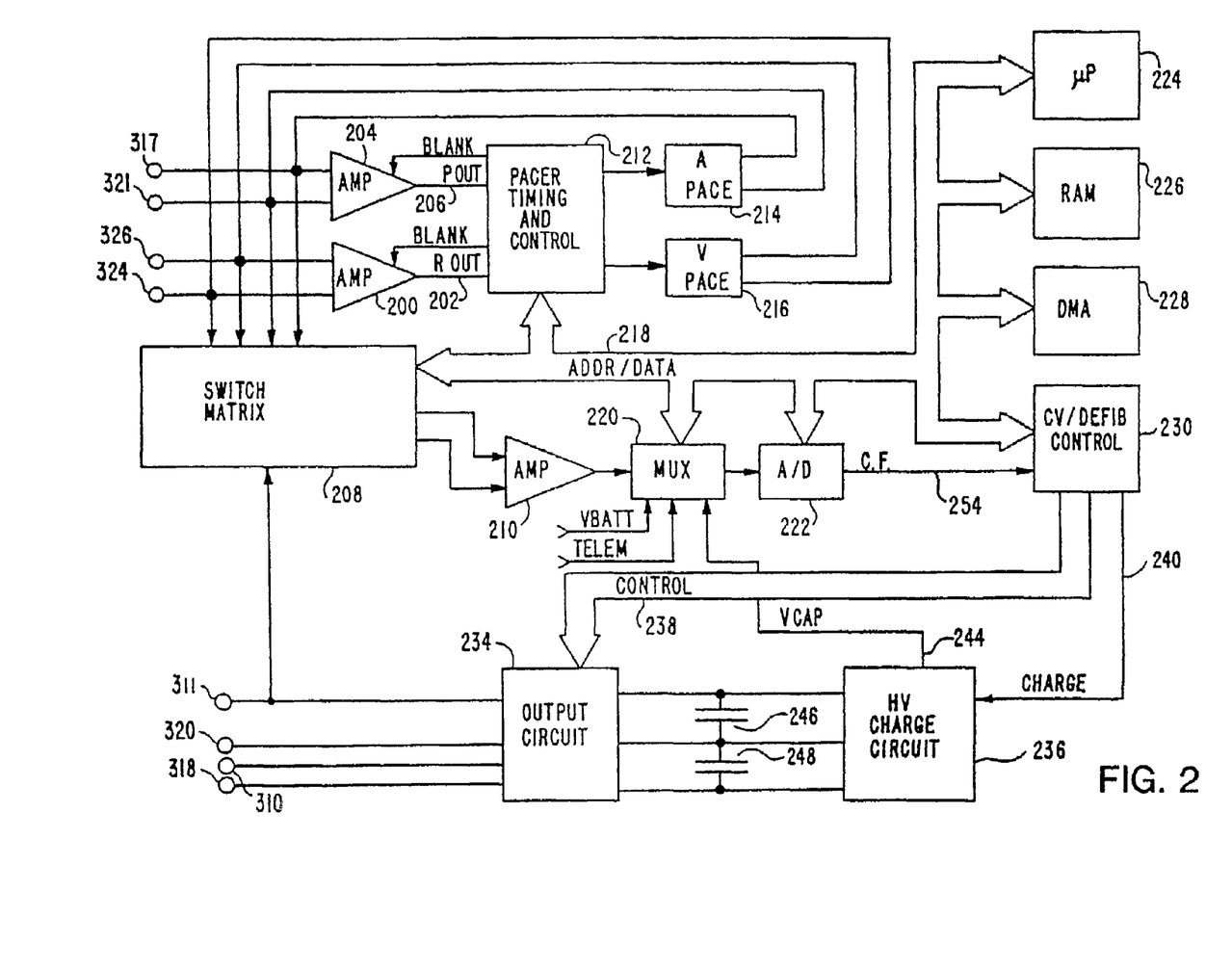
FIG. 2 illustrates a functional schematic diagram of an implantable pacemaker/cardioverter/defibrillator in which the invention may be practiced.

FIG. 2 is a functional schematic diagram of an implantable pacemaker/cardio-verter/defibrillator in which the present invention may be practiced. This diagram should be taken as exemplary of the type of device in which the invention may be embodied, and not as limiting, as it is believed that the invention may generally be practiced in a wide variety of device implementations, including devices providing therapies for treating atrial arrhythmias only and cardioverters and defibrillators that do not provide antitachycardia pacing therapies, as well as devices that deliver additional forms of anti-arrhythmia therapies such as nerve stimulation or drug administration.

The device is provided with a lead system including electrodes, which may be as illustrated in FIG. 1. Alternate lead systems may of course be substituted. If the electrode configuration of FIG. 1 is employed, the correspondence to the illustrated electrodes is as follows. Electrode 311 corresponds to electrode 11, and is the uninsulated portion of the housing of the implantable pacemaker/cardioverter/defibrillator. Electrode 320 corresponds to electrode 20 and is a defibrillation electrode located in the right ventricle. Electrode 310 corresponds to electrode 8 and is a defibrillation electrode located in the coronary sinus. Electrode 318 corresponds to electrode 23 and is a defibrillation electrode located in the superior vena cava. Electrodes 324 and 326 correspond to electrodes 24 and 26, and are used for sensing and pacing in the ventricle. Electrodes 317 and 321 correspond to electrodes 17 and 21 and are used for pacing and sensing in the atrium.

Electrodes 310, 311, 318 and 320 are coupled to high voltage output circuit 234. Electrodes 324 and 326 are coupled to the R-wave amplifier 200, which preferably takes the form of an automatic gain controlled amplifier providing an adjustable sensing threshold as a function of the measured R-wave amplitude. A signal is generated on R-out line 202 whenever the signal sensed between electrodes 324 and 326 exceeds the present sensing threshold.

Electrodes 317 and 321 are coupled to the P-wave amplifier 204, which preferably also takes the form of an automatic gain controlled amplifier providing an adjustable sensing threshold as a function of the measured P-wave amplitude. A signal is generated on P-out line 206 whenever the signal sensed between electrodes 317 and 321 exceeds the present sensing threshold. The general operation of the R-wave and P-wave amplifiers 200 and 204 may correspond to that disclosed in U.S. Pat. No. 5,117,824, by Keimel, et al., issued Jun. 2, 1992, for an Apparatus for Monitoring Electrical Physiologic Signals, incorporated herein by reference in its entirety.

Switch matrix 208 is used to select which of the available electrodes are coupled to wide band (0.5–200 Hz) amplifier 210 for use in digital signal analysis. Selection of electrodes is controlled by the microprocessor 224 via data/address bus 218, which selections may be varied as desired. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm employing any of the numerous signal-processing methods known to the art.

The remainder of the circuitry is dedicated to the provision of cardiac pacing, cardioversion and defibrillation therapies, and, for purposes of the present invention may correspond to circuitry known in the prior art. An exemplary apparatus is disclosed for accomplishing pacing, cardioversion and defibrillation functions as follows. The pacer timing/control circuitry 212 includes programmable digital counters which control the basic time intervals associated with DDD, VVI, DVI, VDD, AAI, DDI and other modes of single and dual chamber pacing well known to the art. Circuitry 212 also controls escape intervals associated with anti-tachyarrhythmia pacing in both the atrium and the ventricle, employing, any anti-tachyarrhythmia pacing therapies known to the art.

Intervals defined by pacer timing/control circuitry 212 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 224, in response to stored data in memory 226 and are communicated to circuitry 212 via address/data bus 218.

Pacer timing/control circuitry 212 also determines the amplitude of the cardiac pacing pulses under control of microprocessor 224.

During pacing, the escape interval counters within pacer timing/control circuitry 212 are reset upon sensing of R-waves and P-waves as indicated by signals on lines 202 and 206, and in accordance with the selected mode of pacing on time-out trigger generation of pacing pulses by pacer output circuits 214 and 216, which are coupled to electrodes 317, 321, 324 and 326. The escape interval counters are also reset on generation of pacing pulses, and thereby control the basic timing of cardiac pacing functions, including anti-tachyarrhythmia pacing.

The durations of the intervals defined by the escape interval timers are determined by microprocessor 224, via data/address bus 218. The value of the count present in the escape interval counters when reset by sensed R-waves and P-waves may be used to measure the durations of R-R intervals, P-P intervals, PR intervals and R-P intervals, which measurements are stored in memory 226 and used in conjunction with the present invention to diagnose the occurrence of a variety of tachyarrhythmias, as discussed in more detail below.

Microprocessor 224 operates as an interrupt driven device, operating under control of programming stored in its read only memory and is responsive to interrupts from pacer timing/control circuitry 212 corresponding to the occurrences of sensed P-waves and R-waves and corresponding to the generation of cardiac pacing pulses and cardioversion/defibrillation pulses. These interrupts are provided via data/address bus 218. Any necessary mathematical calculations to be per-formed by microprocessor 224 and any updating of the values or intervals controlled by pacer timing/control circuitry 212 take place following such interrupts. A portion of the memory 226 (FIG. 4) may be configured as a plurality of recirculating buffers, capable of holding series of measured intervals, which may be analyzed in response to the occurrence of a pace or sense interrupt to determine whether the patient's heart is presently exhibiting atrial or ventricular tachyarrhythmia.

The present invention may employ any tachycardia detection algorithm known to the art to detect the occurrence of tachyarrhythmias. For example, the detection methods disclosed in U.S. Pat. No. 5,545,186 issued to Olson et al for detection of atrial fibrillation and tachycardias may be employed, or the method of U.S. patent application Ser. No. 08/649,145 fled May 14, 1996 for this detection method. The Olson patent and the Gillberg et al. application are hereby incorporated by reference in their entireties. Alternatively, other known detection algorithms for use in conjunction with implantable-atrial cardioverters such as those disclosed in U.S. Pat. No. 5,464,431 issued to Adams et al, U.S. Pat. No. 5,161,527 issued to Nappholz et al, or U.S. Pat. No. 5,107,850 issued to Olive, all incorporated by reference in their entireties may also be employed. A device embodying the present invention may also include the ability to treat ventricular tachyarrhythmias, as discussed above. In the event such capability is desired, any of the prior art ventricular tachyarrhythmia detection methods may be employed, including those in the above cited Olson patent and Gillberg et al application, as well as the detection methods disclosed in U.S. Pat. No. 5,620,471 issued to Duncan, U.S. Pat. No. 4,830,006 issued to Haluska et al., U.S. Pat. No. 4,880,005 issued to Pless et al., and U.S. Pat. No. 5,560,369 issued to McClure et al., all incorporated by reference in their entireties as well. In addition, the device may be configured such that the patient initiates delivery of the therapy by means of an external controller, such that the device may not employ a detection method of its own as a prerequisite to a delivery of therapy. In this context, a patient activator as disclosed in U.S. patent application Ser. No. 08/764,865 by Prieve et al. filed on Dec. 16, 1996, incorporated by reference in its entirety herein may be employed. Alternatively, patient activators of the sort disclosed in U.S. Pat. No. 5,674,249 issued to DeCoriolis et al. or U.S. Pat. No. 4,232,679 issued to Schulman, all incorporated by reference in their entireties may instead be employed. The particular choice of patient activator is not critical to the success of the invention, and any workable method for initiating the delivery of the atrial cardioversion or defibrillation therapy may generally be employed. In the event that an atrial or ventricular tachyarrhythmia is detected, and an anti-tachyarrhythmia pacing regimen is desired, appropriate timing intervals for controlling generation of anti-tachyarrhythmia pacing therapies are loaded from microprocessor 224 into the pacer timing/control circuitry 212, to control the operation of the escape interval counters therein and to define refractory periods during which detection of R-waves and P-waves is ineffective to restart the escape interval counters. Alternatively, circuitry for controlling the timing and generation of anti-tachycardia pacing pulses as described in U.S. Pat. No. 4,577,633, issued to Berkovits et al on Mar. 25, 1986, U.S. Pat. No. 4,880,005, issued to Pless et al on Nov. 14, 1989, U.S. Pat. No. 4,726,380, issued to Vollmann et al on Feb. 23, 1988 and U.S. Pat. No. 4,587,970, issued to Holley et al on May 13, 1986, all of which are incorporated herein by reference in their entireties may also be used.

In the event that generation of a cardioversion or defibrillation pulse is required, microprocessor 224 employs the escape interval counters in circuitry 212 to control timing of such cardioversion and defibrillation pulses, as well as associated refractory periods. In response to the detection of atrial or ventricular fibrillation or tachyarrhythmia requiring a cardioversion pulse, microprocessor 224 activates cardioversion/defibrillation control circuitry 230, which initiates charging of the high voltage capacitors 246, 248 via charging circuit 236, under control of high voltage charging control line 240. The voltage on the high voltage capacitors is monitored via VCAP line 244, which is passed through multiplexer 220 and in response to reaching a predetermined value set by microprocessor 224, results in generation of a logic signal on Cap Full (CF) line 254, terminating charging. Thereafter, timing of the delivery of the defibrillation or cardioversion pulse is controlled by pacer timing/control circuitry 212. Following delivery of the fibrillation or tachycardia therapy the microprocessor then returns the device to cardiac pacing and awaits the next successive interrupt due to pacing or the occurrence of a sensed atrial or ventricular depolarization.

One embodiment of an appropriate system for delivery and synchronization of ventricular cardioversion and defibrillation pulses and for controlling the timing functions related to them is disclosed in more detail in commonly assigned U.S. Pat. No. 5,188,105 by Keimel, issued Feb. 23, 1993, and incorporated herein by reference in its entirety. Any known ventricular cardioversion or defibrillation pulse control circuitry is believed usable in conjunction with the present invention. For example, circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al, cited above, and in U.S. Pat. No. 4,375,817, issued to Engle et al, all incorporated herein by reference in their entireties may also be employed. In addition, high frequency pulse bursts may be delivered to electrodes 317 and 321 to terminate atrial tachyarrhythmias, as described in PCT Patent Publication No. WO95/28987, filed by Duffin et al and PCT Patent Publication No. WO95/28988, filed by Mehra et al, both incorporated herein by reference in their entireties.

In the illustrated device, delivery of cardioversion or defibrillation pulses is accomplished by output circuit 234, under control of control circuitry 230 via control bus 238. Output circuit 234 determines whether a monophasic or biphasic pulse is delivered, whether the housing 311 serves as cathode or anode and which electrodes are involved in delivery of the pulse. An example of output circuitry for delivery of biphasic pulse regimens may be found in the above-cited patent issued to Mehra and in U.S. Pat. No. 4,726,877, incorporated by reference in its entirety.

An example of circuitry that may be used to control delivery of monophasic pulses is set forth in commonly assigned U.S. Pat. No. 5,163,427, by Keimel, issued Nov. 17, 1992, also incorporated herein by reference in its entirety. However, output control circuitry as disclosed in U.S. Pat. No. 4,953,551, issued to Mehra et al on Sep. 4, 1990 or U.S. Pat. No. 4,800,883, issued to Winstrom on Jan. 31, 1989 both incorporated herein by reference in their entireties, may also be used in conjunction with a device embodying the present invention for delivery of biphasic pulses.

In modern implantable cardioverter/defibrillators, the physician programs the particular therapies into the device ahead of time, and a menu of therapies is typically provided. For example, on initial detection of an atrial or ventricular tachycardia, an anti-tachycardia pacing therapy may be selected and delivered to the chamber in which the tachycardia is diagnosed or to both chambers. On redetection of tachycardia, a more aggressive anti-tachycardia pacing therapy may be scheduled. If repeated attempts at anti-tachycardia pacing therapies fail, a higher-level cardioversion pulse may be selected thereafter. Therapies for tachycardia termination may also vary with the rate of the detected tachycardia, with the therapies increasing in aggressiveness as the rate of the detected tachycardia increases. For example, fewer attempts at antitachycardia pacing may be undertaken prior to delivery of cardioversion pulses if the rate of the detected tachycardia is above a preset threshold. The references cited above in conjunction with descriptions of prior art tachycardia detection and treatment therapies are applicable here as well.

In the event that atrial fibrillation is identified, high frequency burst stimulation as discussed above may be employed as the initial attempted therapy. Subsequent therapies may be delivery of high amplitude defibrillation pulses, typically in excess of 5 joules. Lower energy levels may be employed for cardioversion. As in the case of currently available implantable pacemakers/cardioverter/defibrillators, and as discussed in the above-cited references, it is envisioned that the amplitude of the defibrillation pulse may be incremented in response to failure of an initial pulse or pulses to terminate fibrillation. Prior art patents illustrating such pre-set therapy menus of anti-tachyarrhythmia therapies include the above-cited U.S. Pat. No. 4,830,006, issued to Haluska, et al., U.S. Pat. No. 4,726,380, issued to Vollmann et al. and U.S. Pat. No. 4,587,970, issued to Holley et al.

Figure 3:
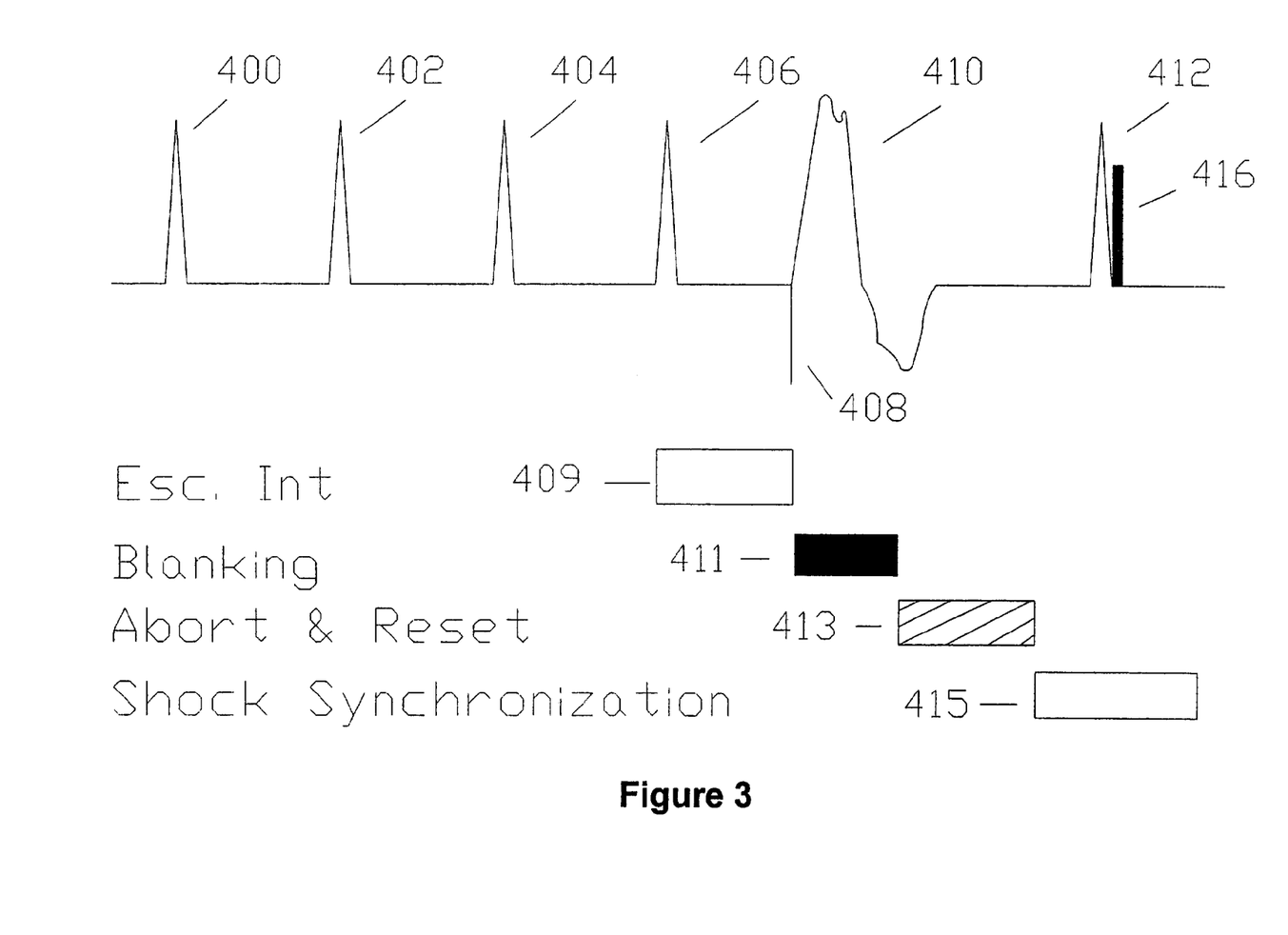
FIG. 3 illustrates the synchronization method used by a device embodying the present invention.

FIG. 3 is a simulated electrogram and timing diagram illustrating the synchronization method of the present invention. When interpreting the simulated electrogram, it should be understood that atrial fibrillation is ongoing. Atrial depolarizations are not illustrated, for the sake of simplicity. A rapid ventricular rhythm, including R-waves 400, 402, 404 and 406 is underway, for example, separated by intervals of less than 400 milliseconds. The device of FIG. 2 measures the six R-R intervals preceding, as well as R-waves 400, 402, 404 and 406 to derive a mean ventricular interval as a reference to determine the percent of decrementation for the paced interval 409 that will cause the R-R prolongation 412. Note that the mean V-R interval (paced to intrinsic R-wave) is scanned in a decrementing fashion (not shown) until a paced interval is found that will produce a forced V-R interval prolongation (410 to 412) that allows for safe delivery of the atrial defibrillation shock. At the expiration of the decremented escape interval 409, a ventricular pacing pulse 408 is delivered, triggering a paced R-wave 410. Simultaneous with delivery of the pacing pulse 408, the device initiates a Blanking period 411 that is programmable from a minimum of 100 to a maximum of 425 milliseconds. The purpose of this blanking period is to prevent the device from sensing the pacing output pulse. An Abort and Reset period 413 programmable between 3 and 560 milliseconds is initiated upon termination of the Blanking period 411. If a ventricular depolarization is sensed within the Abort and Reset period 411, the atrial defibrillation shock is not delivered. Upon expiration of the Abort and Reset period, the Shock Synchronization period 415 begins. A ventricular sensed event within the period 415 will trigger a synchronized atrial defibrillation shock 416.

Delivery of pacing pulse 408 and triggering R-wave 410 causes a delay in the occurrence of the next subsequent R-wave 412 until after expiration of the Blanking period 411, as well as the Abort and Reset period 413. On sensing an R-wave 412 within the Shock Synchronization period 415, the device delivers an atrial cardioversion pulse 416, safely outside the refractory period of R-wave 410. In the event that an R-wave is sensed during the Abort and Reset period 413, after the Blanking period 411, the device will reinitiate the synchronization sequence, measuring the V-R interval separating pacing pulse 408 and the sensed R-wave and defining a new decremented pacing interval based on the V-R interval and preceding R-R intervals that are used to determine a new mean R-R interval. If the device is unable to successfully synchronize using the synchronization method illustrated, it may repeat the synchronization sequence. On failure to successfully deliver a synchronized cardioversion or defibrillation pulse after the final decrement is attained, the device aborts the attempt at cardioversion therapy and returns to normal bradycardia pacing.

The synchronization method of the present invention may be the only synchronization method employed by the device. However, it is anticipated that it more likely will be included in the device along with one or more alternative synchronization methods. The synchronization method of the present invention may be employed, for example, in response to failure to synchronize using an alternative synchronization method or in response to a heart rhythm determined to be inappropriate for employing an alternative synchronization method.

Figure 4:
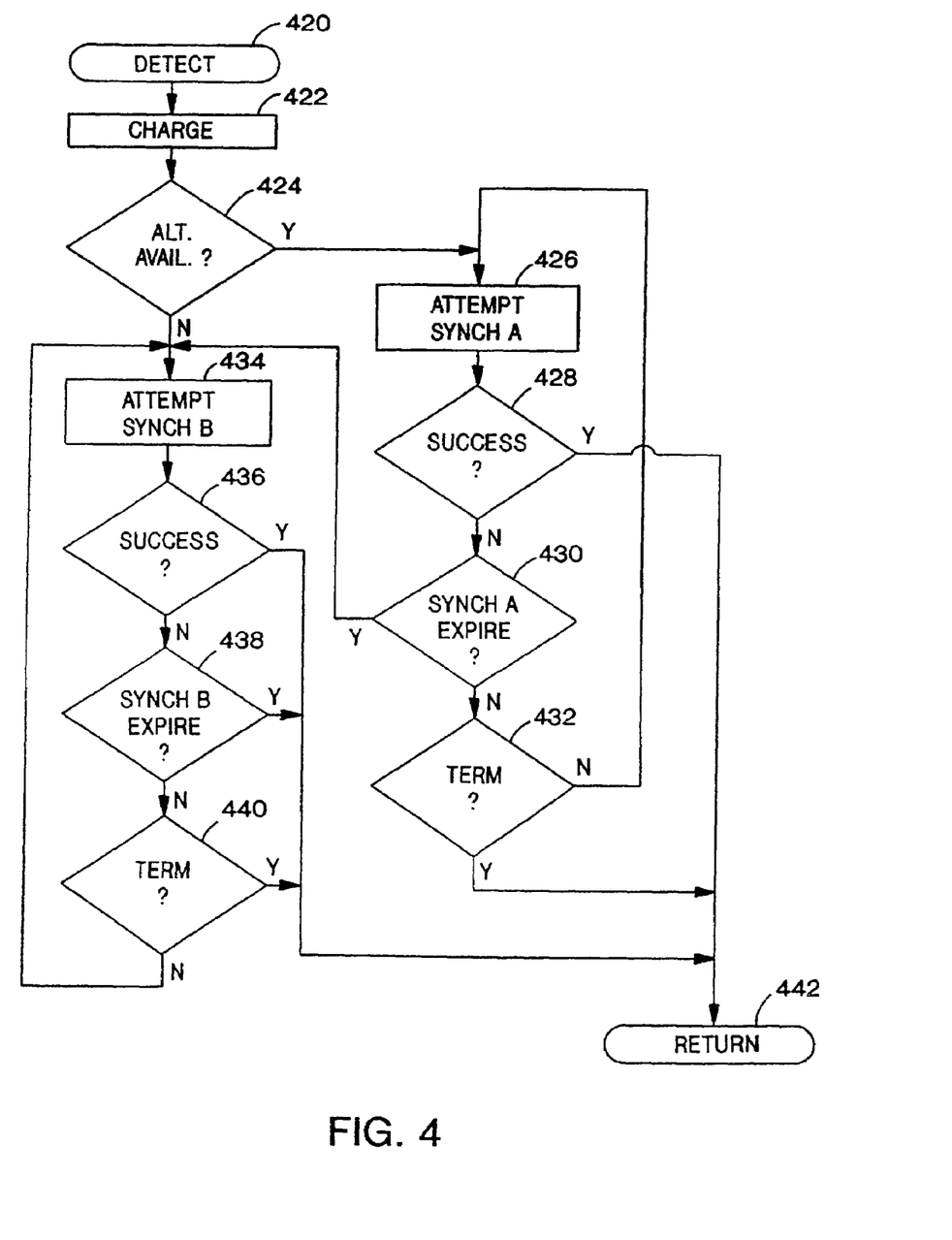
FIG. 4 is a functional flowchart illustrating the operation of the synchronization method according to the present invention.

FIG. 4 is a functional flow chart illustrating a first method of operation of the device of FIGS. 1 and 2 in response to detection of an atrial tachyarrhythmia requiring delivery of a cardioversion or defibrillation pulse. After detection of atrial tachyarrhythmia at 420, the device charges its high voltage output capacitors, and on completion of capacitor charging attempts to deliver a ventricular synchronized atrial cardioversion shock. The device may optionally first attempt synchronization using an alternative method, referred to in FIG. 4 as "Synch A" 426 which may be any of the numerous known synchronization methods for atrial cardioversion. For example, the device may simply define a minimum R-R interval as prerequisite to cardioversion as described in U.S. Pat. No. 5,411,524 issued to Keimel, or may use any of the various other cardioversion mechanisms described in U.S. Pat. No. 5,486,198, U.S. Pat. No. 5,411,525 and U.S. Pat. No. 5,193,536, all incorporated herein by reference in their entireties. If an alternative cardioversion mechanism is not available or is not enabled at 424, the device proceeds immediately to attempt synchronization using the cardioversion synchronization method of the present invention, referred to in FIG. 4 as "Synch B" 434.

Assuming that an alternative cardioversion synchronization method is available at 424, the device attempts to deliver a synchronized atrial cardioversion shock at 426 using the alternative synchronization method. The device continues to attempt to deliver a synchronized atrial cardioversion shock using the alternative synchronization method until expiration of a first maximum time period (e.g. 30 seconds to 3 minutes) or a predetermined number of synchronization attempts (e.g. 2–20) at 430, or until spontaneous termination of the detected atrial tachyarrhythmia at 432. If the device is successful in delivering an atrial cardioversion shock using the alternative synchronization method "Synch A" or if the tachyarrhythmia terminates, the device returns to bradycardia pacing at 442.

If the maximum interval for synchronization employing the alternative synchronization method "Synch A" expires or the maximum number of attempts occur prior to successful delivery of a synchronized atrial cardioversion shock, the device attempts synchronization at 434 using the synchronization method "Synch B" of the present invention. The device continues to attempt to deliver a synchronized cardioversion shock using the method of the present invention until a cardioversion shock is successfully delivered at 436 or a second maximum synchronization time period for synchronization using the method of the present invention (e.g. 30 seconds to 3 minutes) or a predetermined number of synchronization attempts (e.g. 2–20) at 438 or until spontaneous termination of the atrial tachyarrhythmia is detected at 440. Following any of these events, the device returns to bradycardia pacing at 442.

Figure 5:
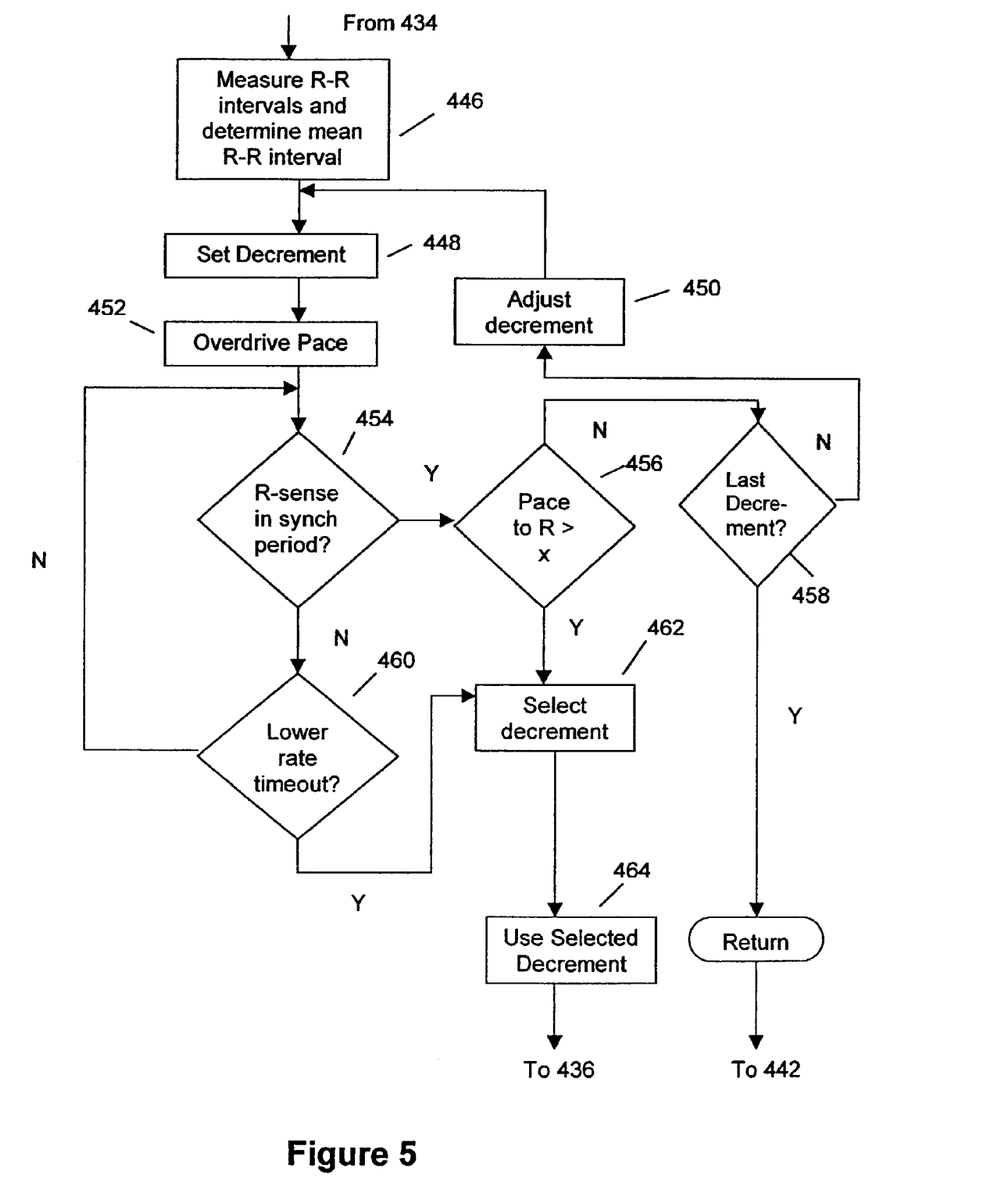
FIG. 5 is a functional flowchart illustrating details of the operation of the synchronization method of the present invention.

FIG. 5 is a functional flow chart illustrating the operation of the scanning, interval decrementation, and synchronization method of the present invention in more detail. The flow chart corresponds to the functional boxes labeled 434 in FIG. 4, and is entered in response to a determination that either the alternative synchronization mechanism "Synch A" is not available or appropriate at 424 or in response to expiration of the maximum time period or maximum number of synchronization attempts available for "Synch A" at 430. In response, the device measures the ten R-R intervals to derive a mean R-R interval at 446. Based on the mean duration of the R-R interval, the device then sets a decrement from this mean for the ventricular escape interval at 446. The intent is to define a ventricular escape interval short enough that it is highly likely to result in an escape interval will expire before the next sensed R-wave. At 452, the device delivers the overdrive pacing output pulse. The device checks at 454 to determine whether a ventricular sensed event has occurred before, during, or after the Shock Synchronization Period. If a ventricular sensed event did occur within the Shock Synchronization Period, the device checks to determine if the V-R (ventricular pace to sensed R) was greater than a certain interval (e.g., 400 ms) at 456. If so, the device will use the decrement at 462 that resulted in the favorable V-R interval at 456 and use this selected decrement at 464 to deliver an atrial shock synchronized to the next R-wave that falls within the Shock Synchronization Period as occurs at 436 in FIG. 4. In response to a sensed R-wave within the synchronization period, the device delivers an atrial cardioversion shock at 436, and indicates that the synchronization method has been successful. The device thereafter returns to bradycardia pacing operation and attempts to determine whether or not the cardioversion shock terminated the detected atrial tachyarrhythmia.

If the V-R interval (ventricular pace to sensed R) was less than a certain interval (e.g., 400 ms) or the sensed R-wave fell into the Abort and Reset Period at 456, the device checks to see if the last decrementation has or has not been used at 458. If not, then the device will decrement (shorten) the R-V interval (sensed R to ventricular pace) by one setting at 450; it uses this setting at 448, and delivers a new overdrive pace at 452. If the last decrementation has been used at 458, the device aborts the operation and returns to bradycardia pacing at 442.

If the ventricular lower rate interval times out at 460 without a prior sensed ventricular depolarization, the device delivers a ventricular pacing pulse at 436 and a cardioversion shock synchronized to the delivered ventricular pacing pulse. The device notes that the synchronization method was successful at 436, and the device returns to bradycardia pacing and attempts to determine whether or not the delivered cardioversion pulse was successful in terminating the detected atrial tachyarrhythmia.

In the above-described embodiments, the device provides a single overdrive ventricular pacing pulse prior to timing the synchronization interval. It should also be understood that the device might alternatively deliver a series of two or more ventricular pacing pulses at the defined escape interval prior to initiating the synchronization interval. In addition, the device is described as providing a ventricular pacing pulse and atrial cardioversion pulse or an atrial cardioversion pulse alone on expiration of a lower rate interval which corresponds to the base pacing rate, which interval typically would be significantly longer than the synchronization interval.

Accordingly, the present invention enables the safe delivery of atrial cardioversion pulses in complex cardiac therapy environments, such as for example, rapid ventricular rates that would prevent a safe atrial cardioversion. Specifically, the invention generally utilizes a resultant R-R interval encountered subsequent to the delivery of a ventricular pacing pulse. The resultant R-R interval is decrementally scanned until an R-R interval is found that will yield a reproducible, forced and sustained R-R interval. The sustenance of interval prolongation assures ventricular deceleration. Specifically, the invention utilizes, preferably, three timing windows wherein ventricular pacing is disabled, an abort and reset period for sensed R-waves and a shock synchronization period in which duration on atrial shock will be synchronized to a sensed R-wave. One of the many aspects of the invention enables a device response that is tailored and specifically matched to a ventricular event occurring within the three timing windows.

The prevailing specific embodiments are illustrative of the practice of the invention. It is to be understood, therefore, that other expedients known to those of skill in the art or disclosed herein may be employed without departing from the invention or the scope of the appended claims. It is therefore to be understood that within the scope of the appended claims, the invention may be practiced otherwise than as specifically described without actually departing from the spirit and scope of the present invention.

What is claimed is:

1. A method of atrial cardioversion/defibrillation comprising:
    measuring R-R intervals and R-waves to determine a mean ventricular interval;
    using said mean as a reference to a percent of decrementation for a paced interval;
    delivering, a ventricular pacing output pulse at the end of a decremented escape interval;
    initiating a blanking period;
    initiating an abort and reset period upon termination of a blanking period;
    beginning a shock synchronization period upon expiration of the abort and reset period; and
    delivering an atrial cardioversion/defibrillation pulse.

2. The method of claim 1, wherein said percent of decrementation causes an R-R prolongation.

3. The method of claim 1, wherein said step of delivering the ventricular pacing pulse includes the further step of triggering a paced R-wave.

4. The method of claim 3, wherein said step of delivering and said further step of triggering cause a delay in the occurrence of a next subsequent R-wave until after expiration of the blanking period and the abort and reset period.

5. The method of claim 1, wherein said step of initiating a blanking period includes the further step of programming a time interval of about between 100 to 425 milliseconds.

6. The method of claim 1, wherein said step of initiating a blanking period is substantially simultaneous with said steps of delivering a ventricular pacing pulse.

7. The method of claim 1, wherein said step of initiating the blanking period includes the step of preventing the cardioverter from sensing said ventricular pacing output pulse.

8. The method of claim 1, wherein said step of initiating an abort and resent period includes the further step of programming a time interval of between about 3 and 560 milliseconds.

9. The method of claim 8, further comprising implementing a ventricular depolarization sensing step to prevent atrial defibrillation shock delivery in the presence of ventricular depolarization within said abort and reset period.

10. The method of claim 1, wherein sensing a ventricular sensed event during the shock synchronization period triggers delivery of the atrial cardioversion/defibrillation pulse.

11. The method of claim 1, wherein said step of delivering a ventricular pacing output includes sensing an R-wave within said synchronization period and delivering an atrial cardioversion pulse, safely outside a refractory period of R-wave.

12. The method of claim 1, wherein said step of initiating an abort and reset period further includes:
    measuring a V-R interval separating a pacing pulse and a sensed R-wave; and
    defining a new decremented pacing interval and preceding R-R intervals that are used to determine a new mean R-R interval.

\* \* \* \* \*

UNITED STATES PATENT AND TRADEMARK OFFICE
CERTIFICATE OF CORRECTION

| | | |
|---|---|---|
| PATENT NO. | : 6,988,000 B2 | Page 1 of 1 |
| APPLICATION NO. | : 10/368871 | |
| DATED | : January 17, 2006 | |
| INVENTOR(S) | : Luc R. Mongeon and Thomas Sinner | |

It is certified that error appears in the above-identified patent and that said Letters Patent is hereby corrected as shown below:

Col. 12, line 13, delete "delivering, a ventricular" and insert in place thereof --delivering a ventricular--

Signed and Sealed this

Seventeenth Day of February, 2009

JOHN DOLL
*Acting Director of the United States Patent and Trademark Office*